US010094828B2

(12) United States Patent
Muench et al.

(10) Patent No.: US 10,094,828 B2
(45) Date of Patent: Oct. 9, 2018

(54) ANTIGEN COMPOSITION FOR DETECTING CHAGAS DISEASE

(71) Applicant: Roche Diagnostics Operations, Inc., Indianapolis, IN (US)

(72) Inventors: Peter Muench, Penzberg (DE); Dieter Roessler, Kirchseeon (DE); Christian Scholz, Penzberg (DE); Barbara Upmeier, Iffeldorf (DE); Toralf Zarnt, Penzberg (DE)

(73) Assignee: Indiana University Research and Technology

( * ) Notice: Subject to any disclaimer, the term of this patent is extended or adjusted under 35 U.S.C. 154(b) by 0 days.

(21) Appl. No.: 15/587,842

(22) Filed: May 5, 2017

(65) Prior Publication Data

US 2017/0248597 A1    Aug. 31, 2017

Related U.S. Application Data

(63) Continuation of application No. PCT/EP2015/075691, filed on Nov. 4, 2015.

(30) Foreign Application Priority Data

Nov. 6, 2014    (EP) .................................... 14192004

(51) Int. Cl.
| | | |
|---|---|---|
| A61K 39/00 | (2006.01) | |
| C07K 14/44 | (2006.01) | |
| G01N 33/569 | (2006.01) | |
| A61K 39/005 | (2006.01) | |
| G01N 33/564 | (2006.01) | |

(52) U.S. Cl.
CPC ..... *G01N 33/56905* (2013.01); *A61K 39/005* (2013.01); *C07K 14/44* (2013.01); *G01N 33/564* (2013.01); *G01N 2333/44* (2013.01); *G01N 2469/20* (2013.01); *G01N 2800/26* (2013.01)

(58) Field of Classification Search
None
See application file for complete search history.

(56) References Cited

U.S. PATENT DOCUMENTS

| 8,329,411 B2 | 12/2012 | Tarleton et al. |
|---|---|---|
| 2010/0196933 A1 | 8/2010 | Kirchhoff et al. |
| 2017/0248597 A1* | 8/2017 | Muench ........... G01N 33/56905 |

FOREIGN PATENT DOCUMENTS

| EP | 0976763 B1 | 11/2003 |
|---|---|---|
| WO | 2009/017736 A1 | 2/2009 |
| WO | 2010/142829 A1 | 12/2010 |
| WO | WO 2016071392 A1 * | 5/2016 |

OTHER PUBLICATIONS

Bottino, Carolina G. et al., Chagas disease-specific antigens: characterization of epitopes in CRA/FRA by synthetic peptide mapping and evaluation by ELISA-peptide assay, BMC Infectious Diseases, 2013, 10 pps., vol. 13, No. 568.
Camussone, Cecilia et al., Comparison of Recombinant Trypanosoma cruzi Peptide Mixtures versus Multiepitope Chimeric Proteins as Sensitizing Antigens for Immunodiagnosis, Clinical and Vaccine Immunology, 2009, pp. 899-905, vol. 16, No. 6.
Chiaramonte, M. G. et al., Polymerase chain reaction reveals Trypanosoma cruzi infection suspected by serology in cutaneous and mucocutaneous leishmaniasis patients, Acta Tropica, 1999, pp. 295-308, vol. 72.
Cotrim, Paulo C. et al., Organization and expression of the gene encoding an immunodominant repetitive antigen associated to the cytoskeleton of Trypanosoma cruzi, Molecular and Biochemical Parasitology, 1995, pp. 89-98, vol. 71.
Da Silveira, José Franco et al., Chagas Disease: recombinant Trypanosoma cruzi antigens for serological diagnosis, Trends in Parasitology, 2001, pp. 286-291, vol. 17, No. 6.
Fernández-Villegas, Ana et al., Short-term follow-up of chagasic patients after benznidazole treatment using multiple serological markers, BMC Infectious Diseases, 2011, 7 pages, vol. 11, No. 206.
International Search Report dated Jan. 28, 2016, in Application No. PCT/EP2015/075691, 5 pages.
Longhi, Silvia A. et al., Short Report: Evaluation of In-House ELISA Using Trypanosoma cruzi Lysate and Recombinant Antigens for Diagnosis of Chagas Disease and Discrimination of Its Clinical Forms, American J. Trop. Med. Hyg., 2012, pp. 267-271, vol. 87, No. 2.
Marcipar, Iván S. and Lagier, Claudia M., Advances in Serological Diagnosis of Chagas' Disease by Using Recombinant Proteins, Current Topics in Tropical Medicine, 2012, pp. 273-298.
Thomas, M. C. et al., Mapping of the antigenic determinants of the T. cruzi kinetoplastid membrane protein-11. Identification of a linear epitope specifically recognized by human Chagasic sera, Clinical and Experimental Immunology, 2001, pp. 465-471, vol. 123.
Umezawa, Eufrosina S. et al., An improved serodiagnostic test for Chagas' disease employing a mixture of Trypanosoma cruzi recombinant antigens, Transfusion, 2003, pp. 91-97, vol. 43.

(Continued)

*Primary Examiner* — Padmavathi Baskar
(74) *Attorney, Agent, or Firm* — Stinson Leonard Street LLP

(57) ABSTRACT

The present invention concerns a composition of polypeptides suitable for detecting antibodies against *Trypanosoma cruzi* (*T. cruzi*) in an isolated biological sample consisting of three polypeptides 1F8, JL7 and Cruzipain. A method of producing a soluble and immunoreactive composition of polypeptides suitable for detecting antibodies against *T. cruzi* using said composition of polypeptides is also part of the invention. Moreover, the invention concerns a method for detecting antibodies specific for *T. cruzi* in an isolated sample wherein a composition of said *T. cruzi* polypeptides is used as well as a reagent kit comprising said composition of *T. cruzi* polypeptides.

3 Claims, 6 Drawing Sheets

Specification includes a Sequence Listing.

(56) References Cited

OTHER PUBLICATIONS

Umezawa, Eufrosina S. et al., Evaluation of Recombinant Antigens for Serodiagnosis of Chagas' Disease in South and Central America, Journal of Clinical Microbiology, 1999, pp. 1554-1560, vol. 37, No. 5.

Valiente-Gabioud, Ariel A. et al., Effect of repetitiveness on the immunogenicity and antigenicity of Trypanosoma cruzi FRA protein, Experimental Parasitology, 2011, pp. 672-679, vol. 127, No. 3.

* cited by examiner

| | Architect Chagas pos: ≥1.0 neg: <0.8 equ: ≥0.8 <1.0 | bioelisa Chagas pos: ≥1.0 neg: <0.9 equ: ≥0.9 <1.0 | NovaLisa Chagas IgG ELISA pos: >1.1 neg: <0.9 equ: 0.9-1.1 | | EcSS-1F8(Cys) | EcSS-1F8 | EcSS-JL7 | EcSS-C-Cruzipain | EcSS-KMP11 | EcSS-PAR2 |
|---|---|---|---|---|---|---|---|---|---|---|
| | S/CO | S/CO | S/CO | | counts | counts | counts | counts | counts | counts |
| normal samples | | | | | | | | | | |
| SN1437 | 0.02 | 0.11 | 0.42 | | 1'100 | 598 | 586 | 605 | 7'507 | 601 |
| SN1438 | 0.02 | 0.07 | 0.15 | | 937 | 577 | 551 | 644 | 6'203 | 584 |
| SN1439 | 0.02 | 0.29 | 0.32 | | 1'002 | 607 | 562 | 591 | 6'598 | 604 |
| SN1440-088 | 0.03 | 0.04 | 0.33 | | 1'437 | 643 | 578 | 608 | 6'930 | 840 |
| SN1440-102 | 0.05 | 0.11 | 0.24 | | 1'170 | 639 | 575 | 628 | 6'442 | 638 |
| | | | | working cut-off | 6'775 | 3'677 | 3'420 | 3'691 | 40'416 | 3'680 |
| Chagas positive samples | | | | | | | | | | |
| SN1440-001 | 4.96 | 2.27 | 2.56 | | 48'452 | 32'476 | 18'211 | 15'602 | 52'237 | 22'798 |
| SN1440-005 | 4.16 | 1.64 | 1.58 | | 32'774 | 22'035 | 13'004 | 11'317 | 39'248 | 16'766 |
| SN1440-036 | 7.08 | 3.30 | 3.22 | | 455'586 | 223'396 | 184'707 | 387'041 | 9'643 | 92'195 |
| SN1440-038 | 1.13 | 2.42 | 2.53 | | 6'109 | 2'986 | 12'829 | 49'203 | 11'545 | 22'237 |
| SN1440-039 | 4.62 | 4.53 | 5.21 | | 34'465 | 15'808 | 14'904 | 3'604 | 22'370 | 57'326 |
| SN1440-040 | 2.02 | 2.57 | 3.35 | | 187'967 | 91'906 | 13'919 | 286'061 | 17'275 | 52'381 |
| SN1440-041 | 7.42 | 3.92 | 3.87 | | 221'327 | 104'871 | 264'421 | 868'701 | 842'535 | 238'532 |
| SN1440-042 | 7.51 | 4.17 | 4.89 | | 156'298 | 84'592 | 120'914 | 39'858 | 1'343'355 | 371'312 |
| SN1440-043 | 3.26 | 6.65 | 5.11 | | 201'414 | 191'169 | 5'842 | 1'037'504 | 50'420 | 83'717 |
| SN1440-048 | 1.32 | 2.08 | 1.52 | | 21'360 | 13'867 | 2'730 | 20'324 | 14'305 | 21'620 |
| SN1440-049 | 8.7 | 5.20 | 4.86 | | 12'246 | 7'456 | 210'951 | 2'853 | 84'879 | 11'269 |
| SN1440-051 | 5.22 | 6.09 | 5.08 | | 63'686 | 30'861 | 3'027 | 130'665 | 14'502 | 608 |
| SN1440-052 | 8.91 | 5.64 | 5.42 | | 232'445 | 123'076 | 583'624 | 258'818 | 168'487 | 308'825 |
| SN1440-053 | 7.96 | 2.02 | 2.96 | | 80'405 | 34'279 | 124'462 | 222'631 | 304'650 | 92'454 |
| SN1440-056 | 3.46 | 2.01 | 2.8 | | 146'099 | 73'718 | 19'383 | 18'024 | 16'241 | 296'171 |
| SN1440-059 | 6.75 | 5.13 | 5.14 | | 40'400 | 21'232 | 66'038 | 203'497 | 169'886 | 179'644 |
| SN1440-060 | 5.78 | 1.65 | 2.78 | | 16'719 | 11'388 | 31'486 | 96'694 | 29'301 | 2'607 |
| SN1440-062 | 1.49 | 1.16 | 2.11 | | 3'578 | 2'326 | 2'563 | 15'807 | 12'298 | 1'603 |
| SN1440-064 | 3.79 | 1.49 | 1.52 | | 2'233 | 989 | 18'156 | 12'972 | 33'650 | 975 |
| SN1440-065 | 3.03 | 1.22 | 3.31 | | 113'580 | 80'128 | 829 | 289'628 | 12'144 | 119'128 |
| SN1440-066 | 4.19 | 1.79 | 3.09 | | 157'875 | 84'471 | 48'032 | 1'253 | 34'667 | 9'027 |
| SN1440-067 | 4.32 | 5.74 | 4.60 | | 79'616 | 35'969 | 17'370 | 49'771 | 11'069 | 7'352 |
| SN1440-068 | 5.22 | 6.26 | 4.96 | | 123'768 | 64'836 | 635 | 36'426 | 7'773 | 104'216 |
| SN1440-069 | 5.8 | 4.70 | 4.51 | | 42'234 | 23'078 | 86'162 | 26'123 | 35'856 | 7'029 |

Table 2

FIG. 1A

|  | Architect Chagas pos: ≥1.0 neg: <0.8 equ: ≥0.8 <1.0 | bioelisa Chagas pos: ≥1.0 neg: <0.9 equ: ≥0.9 <1.0 | NovaLisa Chagas IgG ELISA pos: >1.1 neg: <0.9 equ: ≥0.9 <1.1 |  | EcSS-1F8(Cys) | EcSS-1F8 | EcSS-JL7 | EcSS-C-Cruzipain | EcSS-KMP11 | EcSS-PAR2 |
|---|---|---|---|---|---|---|---|---|---|---|
|  | S/CO | S/CO | S/CO |  | counts | counts | counts | counts | counts | counts |
| normal samples |  |  |  |  |  |  |  |  |  |  |
| SN1437 | 0.02 | 0.11 | 0.42 |  | 1'100 | 598 | 586 | 605 | 7'507 | 601 |
| SN1438 | 0.02 | 0.07 | 0.15 |  | 937 | 577 | 551 | 644 | 6'203 | 584 |
| SN1439 | 0.02 | 0.29 | 0.32 |  | 1'002 | 607 | 562 | 591 | 6'598 | 604 |
| SN1440-088 | 0.03 | 0.04 | 0.33 |  | 1'437 | 643 | 576 | 808 | 6'930 | 840 |
| SN1440-102 | 0.05 | 0.11 | 0.24 |  | 1'170 | 639 | 575 | 628 | 6'442 | 636 |
|  |  |  |  | working cut-off | 6'775 | 3'677 | 3'420 | 3'691 | 40'416 | 3'680 |
| SN1440-070 | 6.89 | 4.14 | 3.41 |  | 542'123 | 245'999 | 78'177 | 356'510 | 196'657 | 586'269 |
| SN1440-072 | 4.17 | 3.96 | 4.36 |  | 600'257 | 336'935 | 650 | 891'092 | 226'707 | 25'817 |
| SN1440-073 | 9.09 | 6.14 | 5.47 |  | 451'166 | 215'016 | 206'137 | 148'809 | 69'560 | 13'960 |
| SN1440-074 | 5.32 | 3.78 | 5.02 |  | 209'170 | 96'274 | 135'625 | 156'648 | 243'190 | 2'628 |
| SN1440-075 | 4.25 | 2.24 | 3.07 |  | 318'706 | 201'624 | 7'207 | 32'371 | 7'172 | 55'879 |
| SN1440-076 | 9.34 | 5.51 | 4.62 |  | 84'348 | 59'501 | 448'436 | 925'497 | 362'008 | 2'054 |
| SN1440-077 | 4.34 | 5.76 | 4.85 |  | 99'024 | 209'093 | 48'470 | 89'687 | 22'336 | 410'143 |
| SN1440-078 | 5.93 | 5.88 | 4.54 |  | 21'333 | 11'102 | 120'347 | 125'395 | 113'643 | 4'441 |
| SN1440-080 | 3.93 | 1.82 | 2.89 |  | 1'620 | 1'941 | 9'977 | 51'020 | 20'660 | 115'783 |
| SN1440-085 | 7.78 | 4.07 | 3.55 |  | 954'122 | 577'147 | 530'003 | 1'021'833 | 364'572 | 689 |
| SN1440-087 | 5.71 | 2.70 | 2.56 |  | 44'798 | 24'397 | 156'646 | 29'148 | 25'607 | 38'762 |
| SN1440-089 | 3.98 | 4.13 | 4.25 |  | 37'204 | 19'339 | 24'319 | 50'081 | 9'369 | 148'658 |
| SN1440-090 | 6.27 | 4.57 | 4.91 |  | 565'712 | 318'705 | 331'548 | 52'090 | 216'308 | 134'700 |
| SN1440-171 | 6.93 | 3.65 | 3.14 |  | 70'934 | 83'536 | 40'374 | 31'682 | 109'165 | 44'593 |
| SN1440-172 | 12.61 | 36.3 | 5.00 |  | 1'073'130 | 664'839 | 1'083'226 | 659'470 | 2'404'438 | 447'883 |
| SN1440-173 | 9.24 | 3.75 | 3.17 |  | 155'715 | 116'429 | 423'787 | 1'119'086 | 174'974 | 140'232 |
| SN1440-174 | 11.52 | 6.71 | 5.42 |  | 289'326 | 222'671 | 921'379 | 602'961 | 220'573 | 510'137 |
| SN1440-175 | 10.37 | 32.7 | 5.07 |  | 471'975 | 251'759 | 1'288'757 | 16'928 | 258'355 | 472'750 |
| SN1443-15 | 4.87 | 6.80 | 4.87 |  | 41'118 | 32'117 | 106'547 | 396'684 | 26'986 | 208'175 |
| SN1443-17 | 9.79 | 5.42 | 5.23 |  | 119'995 | 72'342 | 208'293 | 64'733 | 65'607 | 370'844 |
| SN1443-19 | 9.9 | 7.02 | 4.51 |  | 1'139'104 | 359'908 | 481'323 | 789'054 | 1'704'619 | 475'061 |
| SN1443-20 | 12.47 | 6.66 | 4.62 |  | 467'874 | 363'153 | 1'139'980 | 778'675 | 559'915 | 307'396 |
| SN1443-21 | 4.83 | 5.00 | 4.31 |  | 36'905 | 21'242 | 26'240 | 229'614 | 76'334 | 6'222 |
| SN1443-22 | 5.36 | 2.47 | 1.27 |  | 3'781 | 3'635 | 121'237 | 10'758 | 15'633 | 15'053 |
| SN1443-30 | 10.89 | 6.50 | 4.36 |  | 335'876 | 320'732 | 455'520 | 1'822 | 233'973 | 307'551 |
| SN1443-31 | 12.08 | 5.16 | 4.38 |  | 327'437 | 294'855 | 1'279'326 | 642 | 306'518 | 474'449 |

Table 2 continued

FIG. 1B

| | Architect Chagas pos: ≥1.0 neg: <0.8 equ: ≥0.8 <1.0 | bioelisa CHAGAS pos: ≥1.0 neg: <0.9 equ: ≥0.9 <1.0 | NovaLisa Chagas IgG ELISA pos: >1.1 neg: <0.9 equ: 0.9-1.1 | | EcSS-1F8(Cys) | EcSS-1F8 | EcSS-JL7 | EcSS-C-Cruzipain | EcSS-KMP11 | EcSS-PAR2 |
|---|---|---|---|---|---|---|---|---|---|---|
| | S/CO | S/CO | S/CO | | counts | counts | counts | counts | counts | counts |
| normal samples | | | | | | | | | | |
| SN1437 | 0.02 | 0.11 | 0.42 | | 1'100 | 598 | 586 | 605 | 7'507 | 601 |
| SN1438 | 0.02 | 0.07 | 0.15 | | 937 | 577 | 551 | 644 | 6'203 | 584 |
| SN1439 | 0.02 | 0.29 | 0.32 | | 1'002 | 607 | 562 | 591 | 6'598 | 604 |
| SN1440-088 | 0.03 | 0.04 | 0.33 | | 1'437 | 643 | 576 | 608 | 6'930 | 640 |
| SN1440-102 | 0.05 | 0.11 | 0.24 | | 1'170 | 639 | 575 | 628 | 6'442 | 638 |
| | | | | working cut-off | 6'775 | 3'677 | 3'420 | 3'691 | 40'416 | 3'680 |
| Chagas positive samples | | | | | | | | | | |
| SN1440-126 | 4.19 | 1.17 | 0.982 | | 7'673 | 7'016 | 194'856 | 40'074 | 28'827 | 2'496 |
| SN1440-127 | 3.73 | 0.509 | 1.51 | | 103'139 | 47'508 | 22'868 | 129'597 | 23'518 | 52'202 |
| SN1440-144 | 1.41 | 0.672 | 1.15 | | 93'066 | 40'417 | 7'435 | 8'525 | 7'846 | 3'977 |
| SN1440-146 | 0.45 | 1.12 | 1.30 | | 6'543 | 2'918 | 760 | 16'980 | 8'229 | 2'836 |
| SN1440-153 | 3.46 | 0.900 | 1.54 | | 58'036 | 36'487 | 2'262 | 34'729 | 5'414 | 42'774 |
| SN1440-187 | 1.2 | 1.08 | 0.999 | | 2'470 | 2'964 | 5'030 | 39'342 | 5'159 | 33'478 |
| SN1440-108 | 6.73 | 0.672 | 1.51 | | 86'146 | 35'494 | 135'402 | 497'308 | 95'028 | 29'400 |
| SN1440-109 | 4.86 | 0.619 | 1.25 | | 38'860 | 26'302 | 98'519 | 58'265 | 95'121 | 53'893 |
| SN1440-138 | 3.32 | 0.832 | 1.33 | | 13'117 | 7'826 | 963 | 36'074 | 11'775 | 3'073 |
| SN1443-12 | 0.87 | 4.12 | 4.54 | | 17'691 | 16'913 | 2'869 | 102'131 | 15'226 | 2'401 |
| SN1443-18 | 4.09 | 1.35 | 0.967 | | 12'682 | 14'769 | 67'320 | 8'629 | 79'426 | 1'481 |

Table 3

FIG. 2

|  | bioelisa CHAGAS | ORTHO T.cruzi ELISA Test System | Architect Chagas | Kit variant 1 | | Kit variant 2 | |
|---|---|---|---|---|---|---|---|
|  | S/CO | S/CO | S/CO | counts | S/CO | counts | S/CO |
|  |  |  |  | working cut-off 6'878 |  | working cut-off 6'958 |  |
| 1st International Standard Chagas (TcII) antibody in Human Plasma 09/186 ||||||||
| undiluted | 2.51 | 4.22 | 6.81 | 1'366'831 | 198.72 | 1'349'192 | 193.90 |
| 1:2 | 1.93 | 3.08 | 5.3 | 1'024'432 | 148.94 | 970'755 | 139.51 |
| 1:4 | 1.11 | 2.01 | 4.05 | 597'796 | 86.91 | 576'487 | 82.85 |
| 1:8 | 0.60 | 1.09 | 2.59 | 318'461 | 46.30 | 303'328 | 43.59 |
| 1:16 | 0.30 | 0.61 | 1.35 | 166'318 | 24.18 | 159'465 | 22.92 |
| 1:32 | 0.21 | 0.32 | 0.7 | 84'885 | 12.34 | 82'844 | 11.91 |
| 1:64 | 0.11 | 0.16 | 0.32 | 43'845 | 6.37 | 42'689 | 6.13 |
| 1:128 | 0.11 | 0.11 | 0.17 | 22'407 | 3.26 | 22'019 | 3.16 |
| 1:256 | 0.07 | 0.07 | 0.1 | 11'939 | 1.74 | 11'778 | 1.69 |
| 1:512 | 0.07 | 0.07 | 0.07 | 6'429 | 0.93 | 6'240 | 0.90 |
| 1:1024 | 0.06 | 0.07 | 0.05 | 3'708 | 0.54 | 3'639 | 0.52 |
| 1:2048 | 0.08 | 0.07 | 0.04 | 2'153 | 0.31 | 2'165 | 0.31 |
| 1st International Standard Chagas (TcI) antibody in Human Plasma 09/188 ||||||||
| undiluted | 1.41 | 4.52 | 8.01 | 1'164'757 | 169.34 | 1'137'674 | 163.50 |
| 1:2 | 1.02 | 3.25 | 5.55 | 1'180'761 | 171.67 | 1'118'619 | 160.76 |
| 1:4 | 1.61 | 2.42 | 6.65 | 782'903 | 113.69 | 748'871 | 107.62 |
| 1:8 | 0.28 | 1.49 | 2.76 | 427'264 | 62.12 | 402'905 | 57.90 |
| 1:16 | 0.50 | 0.90 | 4.22 | 216'008 | 31.40 | 207'481 | 29.82 |
| 1:32 | 0.13 | 0.50 | 0.88 | 112'496 | 16.36 | 105'978 | 15.23 |
| 1:64 | 0.21 | 0.26 | 1.57 | 57'264 | 8.33 | 53'856 | 7.74 |
| 1:128 | 0.11 | 0.12 | 0.20 | 29'847 | 4.34 | 28'085 | 4.04 |
| 1:256 | 0.08 | 0.11 | 0.39 | 15'608 | 2.27 | 14'815 | 2.13 |
| 1:512 | 0.09 | 0.10 | 0.12 | 8'471 | 1.23 | 7'985 | 1.15 |
| 1:1024 | 0.08 | 0.08 | 0.08 | 4'644 | 0.68 | 4'501 | 0.65 |
| 1:2048 | 0.08 | 0.08 | 0.06 | 2'755 | 0.40 | 2'627 | 0.38 |

Table 5

FIG. 3

|  | EcSS-1F8 counts | EcSS-JL7 counts | EcSS-C-Cruzipain counts | EcSS-KMP11 counts | 1F8 counts | JL7 counts | C-Cruzipain counts | KMP11 counts |
|---|---|---|---|---|---|---|---|---|
| normal samples |  |  |  |  |  |  |  |  |
| NS1 | 774 | 755 | 770 | 734 | 810 | 699 | 895 | 791 |
| NS2 | 787 | 727 | 780 | 695 | 863 | 700 | 837 | 762 |
| NS3 | 771 | 728 | 776 | 706 | 801 | 692 | 919 | 788 |
| NS4 | 793 | 743 | 767 | 717 | 884 | 693 | 935 | 787 |
| NS5 | 766 | 710 | 790 | 740 | 859 | 683 | 821 | 773 |
| Chagas positive samples |  |  |  |  |  |  |  |  |
| SN1440-012 | 12'343 | 274'446 | 962 | 6'356 | 13'421 | 308'750 | 2'839 | 878 |
| SN1440-015 | 754'601 | 1'832'145 | 73'017 | 906'011 | 1'092'871 | 8'535'719 | 14'145 | 27'035 |
| SN1440-019 | 3'834 | 28'765 | 3'751 | 737 | 4'588 | 33'768 | 2'172 | 850 |
| SN1440-021 | 322'975 | 2'027'719 | 96'809 | 177'678 | 466'754 | 2'606'324 | 15'183 | 8'211 |
| SN1440-028 | 2'903 | 855 | 2'065 | 2'464 | 4'035 | 870 | 1'468 | 882 |
| SN1440-052 | 285'780 | 2'581'290 | 30'334 | 292'415 | 456'103 | 3'131'565 | 16'191 | 7'749 |
| SN1440-059 | 67'769 | 517'248 | 77'374 | 564'540 | 109'072 | 554'033 | 17'482 | 8'182 |
| SN1440-094 | 343'717 | 1'906'041 | 70'667 | 516'112 | 646'033 | 2'396'405 | 19'608 | 10'128 |

Table 6

FIG. 4

|  | EcSS-1F8 0 mM CaCl$_2$ counts | EcSS-1F8 1 mM CaCl$_2$ counts | recovery % |
|---|---|---|---|
| normal samples |  |  |  |
| C143907 | 510 | 534 | 105 |
| C143908 | 508 | 576 | 113 |
| C143909 | 522 | 523 | 100 |
| C143910 | 508 | 535 | 105 |
| C143911 | 506 | 536 | 106 |
| C143912 | 516 | 529 | 103 |
| C143913 | 520 | 518 | 100 |
| C143914 | 524 | 524 | 100 |
| C143915 | 523 | 534 | 102 |
| C143916 | 524 | 536 | 102 |
| C143917 | 532 | 517 | 97 |
| C143918 | 512 | 531 | 104 |
| C143919 | 530 | 535 | 101 |
| C143920 | 510 | 533 | 105 |
| C143921 | 511 | 529 | 104 |
| C143922 | 536 | 554 | 103 |
| Chagas positive samples |  |  |  |
| SN1440-167 | 495'347 | 583'774 | 118 |
| SN1440-168 | 69'328 | 152'274 | 220 |
| SN1440-169 | 146'857 | 254'499 | 173 |
| SN1440-170 | 55'065 | 78'873 | 143 |
| SN1440-171 | 80'354 | 114'591 | 143 |
| SN1440-172 | 467'189 | 449'061 | 96 |
| SN1440-173 | 156'964 | 175'805 | 112 |
| SN1440-174 | 219'415 | 432'535 | 197 |
| SN1440-175 | 368'215 | 418'037 | 114 |
| SN1440-176 | 97'114 | 157'364 | 162 |
| SN1440-177 | 523'141 | 627'085 | 120 |
| SN1440-178 | 479'703 | 534'115 | 111 |
| SN1440-179 | 157'954 | 238'243 | 151 |
| SN1440-180 | 293'502 | 407'658 | 139 |
| SN1440-181 | 357'961 | 467'273 | 131 |
| SN1440-182 | 412'148 | 513'367 | 125 |
| SN1440-183 | 387'962 | 509'267 | 131 |
| SN1440-184 | 83'522 | 178'316 | 213 |
| SN1440-185 | 25'025 | 45'663 | 182 |
| SN1440-186 | 95'164 | 114'718 | 121 |
| SN1440-187 | 2'032 | 4'432 | 218 |
| SN1440-188 | 9'027 | 17'939 | 199 |
| SN1440-189 | 105'216 | 132'977 | 126 |
| SN1440-190 | 145'852 | 200'161 | 137 |
| SN1440-191 | 231'928 | 318'487 | 137 |
| SN1440-192 | 11'881 | 24'312 | 205 |
| SN1440-193 | 23'647 | 24'356 | 103 |
| SN1440-194 | 163'562 | 250'796 | 153 |

Table 7

FIG 5

SEQUENCE LISTING

```
<160> NUMBER OF SEQ ID NOS: 8

<210> SEQ ID NO 1
<211> LENGTH: 211
<212> TYPE: PRT
<213> ORGANISM: Artificial Sequence
<220> FEATURE:
<223> OTHER INFORMATION: Derived from UniProt Q4D1Q2 Trypanosoma cruzi
      1F8 with variation X= Cys, Ala or Ser
<220> FEATURE:
<221> NAME/KEY: misc_feature
<222> LOCATION: (4)..(4)
<223> OTHER INFORMATION: Xaa can be Cys, Ala or Ser
<220> FEATURE:
<221> NAME/KEY: misc_feature
<222> LOCATION: (66)..(66)
<223> OTHER INFORMATION: Xaa can be Cys, Ala or Ser
<220> FEATURE:
```

```
<221> NAME/KEY: misc_feature
<222> LOCATION: (74)..(74)
<223> OTHER INFORMATION: Xaa can be Cys, Ala or Ser
<220> FEATURE:
<221> NAME/KEY: misc_feature
<222> LOCATION: (124)..(124)
<223> OTHER INFORMATION: Xaa can be Cys, Ala or Ser

<400> SEQUENCE: 1
```

| | | | | | | | | | | | | | | | |
|---|---|---|---|---|---|---|---|---|---|---|---|---|---|---|---|
| Met | Gly | Ala | Xaa | Gly | Ser | Lys | Gly | Ser | Thr | Ser | Asp | Lys | Gly | Leu | Ala |
| 1 | | | | 5 | | | | | 10 | | | | | 15 | |
| Ser | Asp | Lys | Asp | Gly | Lys | Asn | Ala | Lys | Asp | Arg | Lys | Glu | Ala | Trp | Glu |
| | | | 20 | | | | | 25 | | | | | 30 | | |
| Arg | Ile | Arg | Gln | Ala | Ile | Pro | Arg | Glu | Lys | Thr | Ala | Glu | Ala | Lys | Gln |
| | | 35 | | | | | 40 | | | | | 45 | | | |
| Arg | Arg | Ile | Glu | Leu | Phe | Lys | Lys | Phe | Asp | Lys | Asn | Glu | Thr | Gly | Lys |
| | 50 | | | | | 55 | | | | | 60 | | | | |
| Leu | Xaa | Tyr | Asp | Glu | Val | His | Ser | Gly | Xaa | Leu | Glu | Val | Leu | Lys | Leu |
| 65 | | | | | 70 | | | | | 75 | | | | | 80 |
| Asp | Glu | Phe | Thr | Pro | Arg | Val | Arg | Asp | Ile | Thr | Lys | Arg | Ala | Phe | Asp |
| | | | | 85 | | | | | 90 | | | | | 95 | |
| Lys | Ala | Arg | Ala | Leu | Gly | Ser | Lys | Leu | Glu | Asn | Lys | Gly | Ser | Glu | Asp |
| | | | 100 | | | | | 105 | | | | | 110 | | |
| Phe | Val | Glu | Phe | Leu | Glu | Phe | Arg | Leu | Met | Leu | Xaa | Tyr | Ile | Tyr | Asp |
| | | 115 | | | | | 120 | | | | | 125 | | | |
| Phe | Phe | Glu | Leu | Thr | Val | Met | Phe | Asp | Glu | Ile | Asp | Ala | Ser | Gly | Asn |
| | 130 | | | | | 135 | | | | | 140 | | | | |
| Met | Leu | Val | Asp | Glu | Glu | Leu | Lys | Arg | Ala | Val | Pro | Lys | Leu | Glu |
| 145 | | | | | 150 | | | | | 155 | | | | | 160 |
| Ala | Trp | Gly | Ala | Lys | Val | Glu | Asp | Pro | Ala | Ala | Leu | Phe | Lys | Glu | Leu |
| | | | | 165 | | | | | 170 | | | | | 175 | |
| Asp | Lys | Asn | Gly | Thr | Gly | Ser | Val | Thr | Phe | Asp | Glu | Phe | Ala | Ala | Trp |
| | | | 180 | | | | | 185 | | | | | 190 | | |
| Ala | Ser | Ala | Val | Lys | Leu | Asp | Ala | Asp | Gly | Asp | Pro | Asp | Asn | Val | Pro |
| | | 195 | | | | | 200 | | | | | 205 | | | |
| Glu | Ser | Ala | | | | | | | | | | | | | |
| | | 210 | | | | | | | | | | | | | |

```
<210> SEQ ID NO 2
<211> LENGTH: 226
<212> TYPE: PRT
<213> ORGANISM: Trypanosoma cruzi

<400> SEQUENCE: 2
```

| | | | | | | | | | | | | | | | |
|---|---|---|---|---|---|---|---|---|---|---|---|---|---|---|---|
| Met | Glu | Gln | Glu | Arg | Arg | Gln | Leu | Leu | Glu | Lys | Asp | Pro | Arg | Arg | Asn |
| 1 | | | | 5 | | | | | 10 | | | | | 15 | |
| Ala | Arg | Glu | Ile | Ala | Ala | Leu | Glu | Glu | Ser | Met | Asn | Ala | Arg | Ala | Gln |
| | | | 20 | | | | | 25 | | | | | 30 | | |
| Glu | Leu | Ala | Arg | Glu | Lys | Lys | Leu | Ala | Asp | Arg | Ala | Phe | Leu | Asp | Gln |
| | | 35 | | | | | 40 | | | | | 45 | | | |
| Lys | Pro | Glu | Gly | Val | Pro | Leu | Arg | Glu | Leu | Pro | Leu | Asp | Asp | Asp | Ser |
| | 50 | | | | | 55 | | | | | 60 | | | | |
| Asp | Phe | Val | Ala | Met | Glu | Gln | Glu | Arg | Arg | Gln | Leu | Leu | Glu | Lys | Asp |
| 65 | | | | | 70 | | | | | 75 | | | | | 80 |
| Pro | Arg | Arg | Asn | Ala | Lys | Glu | Ile | Ala | Ala | Leu | Glu | Glu | Ser | Met | Asn |
| | | | | 85 | | | | | 90 | | | | | 95 | |
| Ala | Arg | Ala | Gln | Glu | Leu | Ala | Arg | Glu | Lys | Lys | Leu | Ala | Asp | Arg | Ala |

```
                    100                 105                 110
Phe Leu Asp Gln Lys Pro Glu Gly Val Pro Leu Arg Glu Leu Pro Leu
                115                 120                 125

Asp Asp Asp Ser Asp Phe Val Ser Met Glu Gln Glu Arg Arg Gln Leu
            130                 135                 140

Leu Glu Lys Asp Pro Arg Arg Asn Val Gln Lys Ile Ala Asp Leu Glu
145                 150                 155                 160

Glu Ser Met Asn Ala Arg Ala Gln Glu Leu Ala Arg Glu Lys Lys Leu
                165                 170                 175

Ala Asp Arg Ala Phe Leu Asp Gln Lys Pro Glu Gly Val Ser Leu Arg
            180                 185                 190

Glu Leu Pro Leu Asp Asp Asp Ser Asp Phe Val Ser Met Glu Gln Glu
                195                 200                 205

Arg Arg Gln Leu Leu Glu Lys Asp Pro Arg Lys Asn Val Gln Ile Val
    210                 215                 220

Ala Asp
225

<210> SEQ ID NO 3
<211> LENGTH: 130
<212> TYPE: PRT
<213> ORGANISM: Trypanosoma cruzi

<400> SEQUENCE: 3

Gly Pro Gly Pro Thr Pro Glu Pro Thr Thr Thr Thr Thr Thr Ser Ala
1               5                   10                  15

Pro Gly Pro Ser Pro Ser Tyr Phe Val Gln Met Ser Cys Thr Asp Ala
            20                  25                  30

Ala Cys Ile Val Gly Cys Glu Asn Val Thr Leu Pro Thr Gly Gln Cys
        35                  40                  45

Leu Leu Thr Thr Ser Gly Val Ser Ala Ile Val Thr Cys Gly Ala Glu
    50                  55                  60

Thr Leu Thr Glu Glu Val Phe Leu Thr Ser Thr His Cys Ser Gly Pro
65                  70                  75                  80

Ser Val Arg Ser Ser Val Pro Leu Asn Lys Cys Asn Arg Leu Leu Arg
                85                  90                  95

Gly Ser Val Glu Phe Phe Cys Gly Ser Ser Ser Gly Arg Leu Ala
            100                 105                 110

Asp Val Asp Arg Gln Arg Arg His Gln Pro Tyr His Ser Arg His Arg
        115                 120                 125

Arg Leu
    130

<210> SEQ ID NO 4
<211> LENGTH: 92
<212> TYPE: PRT
<213> ORGANISM: Trypanosoma cruzi

<400> SEQUENCE: 4

Met Ala Thr Thr Leu Glu Glu Phe Ser Ala Lys Leu Asp Arg Leu Asp
1               5                   10                  15

Ala Glu Phe Ala Lys Lys Met Glu Glu Gln Asn Lys Lys Phe Phe Ala
            20                  25                  30

Asp Lys Pro Asp Glu Ser Thr Leu Ser Pro Glu Met Lys Glu His Tyr
        35                  40                  45

Glu Lys Phe Glu Lys Met Ile Gln Glu His Thr Asp Lys Phe Asn Lys
```

```
            50                  55                  60
Lys Met His Glu His Ser Glu His Phe Lys Ala Lys Phe Ala Glu Leu
 65                  70                  75                  80

Leu Glu Gln Gln Lys Asn Ala Gln Phe Pro Gly Lys
                 85                  90

<210> SEQ ID NO 5
<211> LENGTH: 324
<212> TYPE: PRT
<213> ORGANISM: Trypanosoma cruzi

<400> SEQUENCE: 5

Phe Gln Glu Thr Ser Ala Ile Lys Asp Ala Lys Arg Arg Leu Lys Gln
  1               5                  10                  15

Arg Cys Glu Asp Asp Leu Lys Asn Leu His Asp Ala Ile Gln Lys Ala
                 20                  25                  30

Asp Met Glu Asp Ala Glu Ala Met Lys Arg Phe Ala Thr Gln Lys Glu
                 35                  40                  45

Lys Ser Glu Lys Phe Ile Gln Glu Asn Leu Asp Arg Gln Asp Glu Ala
                 50                  55                  60

Trp Arg Arg Ile Gln Glu Leu Glu Arg Val Leu Gln Arg Leu Gly Thr
 65                  70                  75                  80

Glu Arg Phe Glu Glu Val Lys Arg Arg Ile Glu Glu Asn Asp Arg Glu
                 85                  90                  95

Glu Lys Arg Lys Val Glu Tyr Gln Gln Phe Leu Asp Val Cys Gly Gln
                100                 105                 110

His Lys Lys Leu Leu Glu Leu Ser Val Tyr Asn Cys Asp Leu Ala Met
                115                 120                 125

Arg Cys Ile Gly Met Met Glu Glu Leu Val Ala Glu Gly Cys Ser Ala
                130                 135                 140

Ile Lys Ser Arg His Asp Lys Thr Asn Glu Glu Leu Gly Asp Leu Arg
145                 150                 155                 160

Leu Gln Val His Gln Glu Tyr Leu Glu Ala Phe Arg Arg Leu Tyr Lys
                165                 170                 175

Thr Leu Gly Gln Leu Val Tyr Lys Lys Glu Lys Arg Leu Glu Glu Ile
                180                 185                 190

Asp Arg Asn Ile Arg Thr Thr His Ile Gln Leu Glu Phe Ala Ile Glu
                195                 200                 205

Thr Phe Asp Pro Asn Ala Lys Lys His Ser Asp Ala Lys Lys Glu Leu
                210                 215                 220

Tyr Lys Leu Arg Ala Gln Val Glu Glu Leu Glu Met Leu Lys Asp
225                 230                 235                 240

Lys Met Ala Gln Ala Leu Glu Met Phe Gly Pro Thr Glu Asp Ala Leu
                245                 250                 255

Asn Gln Ala Gly Ile Glu Phe Val His Pro Ala Glu Val Glu Asp
                260                 265                 270

Gly Asn Leu Thr Arg Arg Ser Lys Met Val Glu Tyr Arg Ala His Leu
                275                 280                 285

Ala Lys Gln Glu Glu Val Lys Ile Ala Ala Glu Arg Glu Glu Leu Lys
                290                 295                 300

Arg Ser Lys Thr Leu Gln Ser Gln Tyr Arg Gly Lys Thr Val Gln
305                 310                 315                 320

Gln Ile Thr Gln
```

```
<210> SEQ ID NO 6
<211> LENGTH: 196
<212> TYPE: PRT
<213> ORGANISM: Escherichia coli

<400> SEQUENCE: 6
```

Met Lys Val Ala Lys Asp Leu Val Val Ser Leu Ala Tyr Gln Val Arg
1               5                   10                  15

Thr Glu Asp Gly Val Leu Val Asp Glu Ser Pro Val Ser Ala Pro Leu
            20                  25                  30

Asp Tyr Leu His Gly His Gly Ser Leu Ile Ser Gly Leu Glu Thr Ala
        35                  40                  45

Leu Glu Gly His Glu Val Gly Asp Lys Phe Asp Val Ala Val Gly Ala
    50                  55                  60

Asn Asp Ala Tyr Gly Gln Tyr Asp Glu Asn Leu Val Gln Arg Val Pro
65                  70                  75                  80

Lys Asp Val Phe Met Gly Val Asp Glu Leu Gln Val Gly Met Arg Phe
                85                  90                  95

Leu Ala Glu Thr Asp Gln Gly Pro Val Pro Val Glu Ile Thr Ala Val
            100                 105                 110

Glu Asp Asp His Val Val Val Asp Gly Asn His Met Leu Ala Gly Gln
        115                 120                 125

Asn Leu Lys Phe Asn Val Glu Val Val Ala Ile Arg Glu Ala Thr Glu
    130                 135                 140

Glu Glu Leu Ala His Gly His Val His Gly Ala His Asp His His His
145                 150                 155                 160

Asp His Asp His Asp Gly Cys Cys Gly His Gly His Asp His Gly
                165                 170                 175

His Glu His Gly Gly Glu Gly Cys Cys Gly Gly Lys Gly Asn Gly Gly
            180                 185                 190

Cys Gly Cys His
        195

```
<210> SEQ ID NO 7
<211> LENGTH: 23
<212> TYPE: PRT
<213> ORGANISM: Artificial Sequence
<220> FEATURE:
<223> OTHER INFORMATION: glycine-rich linker sequence

<400> SEQUENCE: 7
```

Gly Gly Gly Ser Gly Gly Gly Ser Gly Gly Gly Ser Gly Gly Gly Ser
1               5                   10                  15

Gly Gly Gly Ser Gly Gly Gly
            20

```
<210> SEQ ID NO 8
<211> LENGTH: 15
<212> TYPE: PRT
<213> ORGANISM: Artificial Sequence
<220> FEATURE:
<223> OTHER INFORMATION: hexa-histidine tag

<400> SEQUENCE: 8
```

Gly Gly Gly Ser Gly Gly Gly Leu Glu His His His His His His
1               5                   10                  15

ANTIGEN COMPOSITION FOR DETECTING CHAGAS DISEASE

CROSS-REFERENCE TO RELATED APPLICATIONS

This application is a continuation of International Application No. PCT/EP2015/075691 filed Nov. 4, 2015, which claims priority to European Application No. 14192004.1 filed Nov. 6, 2014, the disclosures of which are hereby incorporated by reference in their entirety.

BACKGROUND

Chagas disease is a tropical parasitic disease caused by the flagellate protozoan *Trypanosoma cruzi*. *T. cruzi* is commonly transmitted to humans and other mammals by an insect vector, the blood-sucking "kissing bugs" of the subfamily Triatominae (family Reduviidae; in German: "Raubwanzen"). The disease may also be spread through blood transfusion and organ transplantation, ingestion of food contaminated with parasites, and from a mother to her fetus.

*Trypanosoma cruzi* appears in different forms and development stages. The reproducing form is called epimastigote which is adapted just after the kissing bug has taken a blood meal on an infected animal including humans. The epimastigotes move onto the rectal cell wall of the bug. The bug transfers the pathogen via its feces to the next host in a subsequent blood meal where the bug defecates. The infectious form is called trypomastigote and enters the human body through the bite wound. The trypomastigote can therefore be found in human blood. A further form found e.g. in the cytoplasma of heart muscle cells is called amastigote or micromastigote. During the life cycle of *T. cruzi* the amastigote changes to trypomastigote which can be sucked in at the next meal by a kissing bug.

The symptoms of Chagas disease vary over the course of an infection. Often there is an acute phase followed by a chronic phase. There can also be a latent phase after infection. Each phase can be symptom free or life-threatening. In the early, acute stage, symptoms are generally mild and usually produce no more than local swelling at the site of infection. The initial acute phase is responsive to antiparasitic treatments, with 60-90% cure rates. After 4-8 weeks, individuals with active infections enter the chronic phase of Chagas disease that is asymptomatic for 60-80% of chronically infected individuals through their lifetime. During the chronic phase, some patients develop cardiac complications leading to an enlarged heart, heart failure, altered heart rate and sudden death. Also intestinal complications leading to difficulties with eating or passing stool are typical of the chronic stage.

The antiparasitic treatments also appear to delay or prevent the development of disease symptoms during the chronic phase of the disease, but according to the U. S. Centers for Disease Control and Prevention the average life-time risk of developing one or more of these complications is about 30% which means that these chronically infected individuals will still eventually develop life-threatening heart and digestive system disorders. The currently available antiparasitic treatments for Chagas disease are benznidazole and nifurtimox, which can cause temporary side effects in many patients including skin disorders, brain toxicity, and digestive system irritation.

Chagas disease mainly appears in poor, rural areas of Mexico, Central America, and South America; very rarely, the disease has been found in the Southern United States. However, blood donors are screened for infection with *Trypanosoma cruzi* by in vitro diagnostic methods in these countries.

Today several serologic diagnostic methods are available to detect infections with *T. cruzi*, e.g. detection of antibodies against *T. cruzi* by indirect immunofluorescence, indirect hemagglutination, complement fixation, immunoblot techniques and ELISAs. Also methods of molecular biology (e.g. PCR) and elaborate xenodiagnostic methods are applied. In xenodiagnostics a vector-transmitted infection a laboratory-reared, pathogen-free insect (here: the kissing bug) is allowed to suck blood from a patient. The intestinal contents of the insect are then examined for the presence of the pathogen (here: *Trypanosoma cruzi*).

Each of these methods shows its own weaknesses and strengths with regard to sensitivity and specificity and accordingly there is no gold standard method available so far.

In the beginning of Chagas assay development for detection of antibodies native antigen lysates were applied and are still being used. However, using lysates only one of the three development stages of *T. cruzi* is represented in this antigen composition so that there is a certain likelihood to miss infections of the two other stages. More modern assays apply mixtures of recombinant antigens, representing all stages of *T. cruzi* infection.

When native antigen lysates are used the diagnostic assay often faces problems in specificity and cross-reactivities observed in samples of patients that have been infected by *Leishmania*, another parasite. In addition, the production of antigen lysates leads to considerable lot-to-lot variation because of the complex antigen composition of *T. cruzi*. Moreover, very often rare reagents base on native lysates show a weak sensitivity as some lysates do not contain at all or do not contain sufficient antigens of all life cycle stages.

By applying recombinant antigens the above challenges can be circumvented or avoided. However, commercially available assay kits for detecting Chagas disease which are based on recombinant antigen compositions show considerable differences with respect to sensitivity and specificity so that customers, i.e. commercial or clinical labs or blood screening units, often have to use several kits in parallel to obtain reliable results. As a consequence a decision on whether a patient's sample is reactive or not is based on a majority of positive or negative results obtained for the same sample by several kits based on different antigen compositions. It is obvious that this time-consuming procedure of applying multiple diagnostic tests does not make sense economically as it leads to an increase of lab equipment and personal, time, workload and costs.

Serological assays for detecting antibodies against *Trypanosoma cruzi* antigens have been widely described in prior art literature, for review see for example Silveira et al. Trends in Parasitology 2001, Vol. 17 No. 6. *T. cruzi* recombinant antigens relevant for serodiagnosis have been isolated by several laboratories. Several of these genes have tandemly repeated sequences. Due to the extremely large number of antigenic proteins expressed by *Trypanosoma cruzi* (approximately 23000 predicted protein coding sequences and pseudogenes in public data bases) the number of possible combinations of antigens for an immunoassay is enormously huge. Although methods for recombinant production have been known for decades it still remains a challenge to find out which antigens are required to set up a diagnostic assay. Choosing suitable antigens for an immunodiagnostic assay one has to bear in mind to consider antigens of all life cycle stages of the pathogen and also apply antigens against which antibodies can be found for all stages of infection (acute, window and chronic phase). At the same time the number of antigens should not exceed about 5 or 10 because of technical considerations (e.g. lack of solubility and stability, unwanted cross-reactions leading to quenching of signals, avoidance of cross-reactivity to e.g. *Leishmania*) and also economic considerations as each antigen in addition needs to be fully developed, evaluated and produced in large scale. According to Silveria et al. (supra) commercially available assays often use a combination of six or seven different *T. cruzi* antigens, sometimes also in combination of shorter synthetic peptides derived from *T. cruzi* full length antigens.

Another approach to provide a highly sensitive diagnostic test is based on a multicomponent assay applying a high number of various kinds of *T. cruzi* antigens that have been coated individually on separate beads. WO 2009/017736 and U.S. Pat. No. 8,329,411 disclose a device and a method for detecting an infection by *Trypanosoma cruzi* in a biological sample. This set-up includes 16 different proteins (selected from initially 59 candidate proteins, acting as antigens) that have to be coated individually on labeled beads providing an array-like diagnostic tool. Antibodies, if present in the sample, bind to these coated proteins. Consequently the bound antibodies are detected by binding of a labeled secondary antibody to the sample antibodies. While this procedure makes sense for a research approach the high number of antigens leading to large production costs is too costly to be used as a routine assay in a commercial or clinical laboratory.

In summary, the immunoassays for detecting *T. cruzi* antibodies in samples from infected individuals known in the art apply a high number of different antigens to achieve high sensitivity and specificity. A true gold standard and economically affordable assay is still not available.

The problem therefore can be seen in providing a diagnostic composition and method that overcomes the disadvantages with respect to reproducibility, sensitivity and specificity of the prior art assays for detecting infections with *Trypanosoma cruzi*.

The problem is solved by the current invention as specified in the claims.

SUMMARY OF THE INVENTION

The present invention concerns a composition of polypeptides suitable for detecting antibodies against *Trypanosoma cruzi* (*T. cruzi*) in an isolated biological sample comprising polypeptides 1F8, JL7 and at least one of the polypeptides selected from the group consisting of Cruzipain, KMP-11 and PAR2. A further aspect of the invention is a composition of polypeptides suitable to the detection of *T. cruzi* antibodies wherein polypeptide 1F8 comprises SEQ ID NO. 1, polypeptide JL7 comprises SEQ ID NO. 2 and the at least one of the polypeptides selected from the group consisting of Cruzipain, KMP-11 and PAR2 comprises at least one sequence selected from the group consisting of SEQ ID NO. 3 (Cruzipain), SEQ ID NO. 4 (KMP-11) and SEQ ID NO. 5 (PAR2). In particular the invention focuses on a composition of polypeptides consisting of three recombinantly or synthetically produced polypeptides specific for *Trypanosoma cruzi*, wherein said polypeptides are 1F8, JL7 and Cruzipain. The polypeptides in said composition are 1F8 comprising SEQ ID NO. 1, polypeptide JL7 comprising SEQ ID NO. 2 and Cruzipain, comprising SEQ ID NO. 3.

In another embodiment the three *T. cruzi* specific polypeptides 1F8, J17 and Cruzipain present in said composition of polypeptides consist of SEQ ID NOs. 1, 2 and 3, respectively.

Another embodiment concerns a method of producing a soluble and immunoreactive composition of the above-described polypeptides suitable for detecting antibodies against *Trypanosoma cruzi* in an isolated sample. The use of said composition of polypeptides in an in vitro diagnostic assay for the detection of *T. cruzi* specific antibodies is also part of the invention.

Moreover, the invention concerns a method for detecting antibodies specific for *Trypanosoma cruzi* in an isolated sample wherein a composition of said *Trypanosoma cruzi* polypeptides is used as well as a reagent kit comprising said composition of *Trypanosoma cruzi* polypeptides.

Summary of the Disclosed Amino Acid Sequences

SEQ ID NO. 1 shows *T. cruzi* protein 1F8 (UniProt entry Q4D1Q2), also known as FCaBP, Tc24 or Tc28; full descriptive name: flagellar calcium binding protein 3. SEQ ID NO. 1 shows amino acid positions 1-211. According to the invention cysteine residues can be replaced by alanine (A) or serine (S) in order to avoid incorrect folding due to the formation of intramolecular disulfide bridges. Therefore, all positions in which a cysteine (C) naturally appears—in this case four positions—are labeled by an X; X=C, A or S.

```
MGAXGSKGST SDKGLASDKD GKNAKDRKEA WERIRQAIPR

EKTAEAKQRR IELFKKFDKN ETGKLXYDEV HSGXLEVLKL

DEFTPRVRDI TKRAFDKARA LGSKLENKGS EDFVEFLEFR

LMLXYIYDFF ELTVMFDEID ASGNMLVDEE ELKRAVPKLE

AWGAKVEDPA ALFKELDKNG TGSVTFDEFA AWASAVKLDA

DGDPDNVPES A
```

SEQ ID NO. 2 shows a partial sequence of *T. cruzi* protein JL7 (UniProt entry Q4CS87), also known as FRA, Ag1, H49; full descriptive name: calpain cysteine peptidase, putative. SEQ ID NO. 2 shows amino acid positions 62-287 of the above UniProt database entry, resulting in a polypeptide with a length of 226 amino acids. The full length protein comprises amino acids 1 to 1275.

```
MEQERRQLLE KDPRRNAREI AALEESMNAR AQELAREKKL

ADRAFLDQKP EGVPLRELPL DDDSDFVAME QERRQLLEKD

PRRNAKEIAA LEESMNARAQ ELAREKKLAD RAFLDQKPEG

VPLRELPLDD DSDFVSMEQE RRQLLEKDPR RNVQKIADLE

ESMNARAQEL AREKKLADRA FLDQKPEGVS LRELPLDDDS

DFVSMEQERR QLLEKDPRKN VQIVAD
```

SEQ ID NO. 3 shows a partial sequence of *T. cruzi* protein Cruzipain (UniProt entry Q9TW51), also known as Cruzain, gp51/57, Ag 163B6; full descriptive name: major cysteine proteinase. SEQ ID NO. 3 shows amino acid positions 6-135 of the UniProt database entry, resulting in a polypeptide with a length of 130 amino acids, also called C-Cruzipain. The full length protein comprises amino acids 1 to 135.

```
GPGPTPEPTT TTTTSAPGPS PSYFVQMSCT DAACIVGCEN

VTLPTGQCLL TTSGVSAIVT CGAETLTEEV FLTSTHCSGP

SVRSSVPLNK CNRLLRGSVE FFCGSSSSGR LADVDRQRRH

QPYHSRHRRL
```

SEQ ID NO. 4 shows a partial sequence of *T. cruzi* protein KMP-11 (UniProt entry Q9U6Z1), full descriptive name kinetoplastid membrane protein 11. This protein comprises amino acid positions 1 to 92.

```
MATTLEEFSA KLDRLDAEFA KKMEEQNKKF FADKPDESTL

SPEMKEHYEK FEKMIQEHTD KFNKKMHEHS EHFKAKFAEL

LEQQKNAQFP GK
```

SEQ ID NO. 5 shows a partial sequence of *T. cruzi* protein PAR2 (UniProt entry Q01530), also known as PFR2; full descriptive name: major paraflagellar rod protein. SEQ ID NO. 5 shows the C-terminal part (C-PAR2) of PAR2, i.e. amino acid positions 277-600 of the UniProt database entry, resulting in a polypeptide with a length of 324 amino acids. The full length protein comprises amino acids 1 to 600.

```
FQETSAIKDA KRRLKQRCED DLKNLHDAIQ KADMEDAEAM

KRFATQKEKS EKFIQENLDR QDEAWRRIQE LERVLQRLGT

ERFEEVKRRI EENDREEKRK VEYQQFLDVC GQHKKLLELS

VYNCDLAMRC IGMMEELVAE GCSAIKSRHD KTNEELGDLR

LQVHQEYLEA FRRLYKTLGQ LVYKKEKRLE EIDRNIRTTH

IQLEFAIETF DPNAKKHSDA KKELYKLRAQ VEEELEMLKD

KMAQALEMFG PTEDALNQAG IEFVHPAEEV EDGNLTRRSK

MVEYRAHLAK QEEVKIAAER EELKRSKTLQ SQQYRGKTVQ QITQ
```

SEQ ID NO. 6 represents the complete *E. coli* SlyD amino acid sequence (196 amino acid residues) which is also accessible via ID P0A9K9 in the UniProt database. When SlyD is used as a chaperone fusion partner for the *T. cruzi* polypeptides according to the invention, in an embodiment a C-terminally truncated version of *E. coli* SlyD spanning amino acid residues 1-165 of the sequence listed below is used. In another embodiment (as applied in example 1), a tandem version of two SlyD units is added to the N-terminal end of the polypeptides according to the invention. To facilitate cloning and re-folding after expression of a resulting fusion polypeptide these two SlyD units may be separated by a linker sequence as shown in SEQ ID NO. 7.

```
MKVAKDLVVS LAYQVRTEDG VLVDESPVSA PLDYLHGHGS

LISGLETALE GHEVGDKFDV AVGANDAYGQ YDENLVQRVP

KDVFMGVDEL QVGMRFLAET DQGPVPVEIT AVEDDHVVVD

GNHMLAGQNL KFNVEVVAIR EATEEELAHG HVHGAHDHHH

DHDHDGCCGG HGHDHGHEHG GEGCCGGKGN GGCGCH
```

SEQ ID NO. 7 shows the amino acid sequence of the glycine-rich spacer (comprising triple glycine units separated by a serine) that can be used as a flexible, soluble and protease-resistant spacer or linker between fused polypeptide moieties.

```
GGGSGGGSGG GSGGGSGGGS GGG
```

SEQ ID NO. 8 shows a hexa-histidine tag that can be added to the N-terminal or in another embodiment to the C-terminal end of the polypeptides according to the invention. The tag is used to facilitate protein purification and refolding.

```
GGGSGGGLEH HHHHH
```

BRIEF DESCRIPTION OF THE FIGURES

FIG. 1A contains Table 2 showing the experimental results for the detection of anti-*T. cruzi* antibodies in human sera by using recombinant *T. cruzi* antigen variants in comparison with three commercially available Chagas assays (see also example 4). For the Architect Chagas assay a sample is considered as positive (i.e. containing *T. cruzi* antibodies) if the signal to cut-off value (S/CO) is ≥1.0; as negative (no *T. cruzi* antibodies) if the S/CO value is <0.8 and as "equ" if the S/CO value is ≥0.8 and <1.0. "equ" means equivocal (or intermediate), i.e. results are in the grey zone. Depending on the commercial provider's instructions these "equ" samples need to be confirmed by one or two additional assays in order to receive a reliable final result (majority decision). Corresponding S/CO values are shown for Biolisa Chagas and Novalis Chagas IgG ELISA. For the polypeptides according to the invention absolute measured counts (Cobas® e601 analyzer, Roche Diagnostics GmbH, Example 4) and individual cut-off-values are shown for each antigen.

FIG. 1B is Table 2 continued from FIG. 1A.

FIG. 2 (Table 3), containing results of specimen tested with three commercially available Chagas assays for the detection of anti-*T. cruzi* antibodies in human sera in comparison with the results using individual recombinant *T. cruzi* antigen variants according to the invention (see also example 4).

FIG. 3 (Table 5) shows experimental data of example 6 concerning the sensitivity of recombinant *T. cruzi* antigen mixtures in comparison with commercial anti-Chagas assays.

FIG. 4 (Table 6) shows a comparison of the immunological reactivity of recombinant *T. cruzi* antigens with and without chaperone fusion (see also example 7).

FIG. 5 (Table 7) shows experimental data on the calcium dependent reactivity of 1F8 (example 8).

DETAILED DESCRIPTION OF THE INVENTION

As explained in the background section the immunoassays known in prior art for detecting *T. cruzi* antibodies in samples from infected individuals use a high number of different antigens to achieve high sensitivity and specificity. Mostly, the decision on whether a patient is infected or not is based on a majority of results of different immunoassays. So far, there is no gold standard and economically affordable assay available.

Surprisingly, by using a composition or mixture of *Trypanosoma cruzi* specific antigens comprising 1F8, JL7 and at least one of the polypeptides selected from the group consisting of Cruzipain, KMP-11 and PAR2 we have been able to provide a diagnostic composition and method that overcomes the disadvantages of the prior art. The novel composition is comparable or even superior with respect to reproducibility, sensitivity and specificity for detecting antibodies against *Trypanosoma cruzi* in an isolated patient sample. In addition, only three *Trypanosoma cruzi* specific antigens are necessary to generate a composition or kit for reliably detecting *T. cruzi* specific antibodies. The composition comprises at least three, four or five *T. cruzi* polypeptides. In an embodiment, the number of *T. cruzi* specific polypeptides is between three and five; in a further embodiment three polypeptides, i.e. 1F8, JL7 and at least one of the polypeptides selected from the group consisting of Cruzipain, KMP-11 and PAR2. In a further embodiment the composition consists of three *Trypanosoma cruzi* specific antigens 1F8, JL7 and Cruzipain. A further embodiment is a composition comprising 1F8, JL7, Cruzipain and KMP-11. In another embodiment the composition consists of 1F8, JL7, Cruzipain and KMP-11. In yet another embodiment the composition consists of polypeptides disclosed in SEQ ID NO. 1 (1F8), SEQ ID NO. 2 (JL7), and SEQ ID NO. 3 (Cruzipain).

The terms *Trypanosoma cruzi* (=*T. cruzi*) specific antigen, *T. cruzi* specific polypeptide, *T. cruzi* polypeptide and *T. cruzi* antigen can be used synonymously and each refer to a polypeptide sequence that can be found in any naturally occurring *T. cruzi* strain accessible through an international protein database such as UniProt. In the current invention the amino acid chains of applied antigen sequences show a range of lengths between about 90 amino acids (KMP-11) and up to about 400 amino acids (C-PAR2). In an embodiment, the length of each *T. cruzi* antigen is within this range.

As can be seen in Example 4, Table 2 (FIGS. 1A and 1B), the individual *T. cruzi* polypeptides comprising 1F8, JL7, Cruzipain, KMP-11 or PAR2 peptide sequences all exhibit significant antigenicity in an immunoassay when each polypeptide is used as an individual single antigen. However, this example also shows that the reactivity of the individual *T. cruzi* antigen strongly depends on the individual patient serum. There are always some samples that are not detected by using a single antigen. This finding corresponds well to the comparison with commercial Chagas assays. Looking at Table 3 (FIG. 2), one can see that there is also no single commercial assay (each of which uses at least four to ten different recombinant *T. cruzi* specific antigens) that detects all reactive samples. In order to reliably detect *T. cruzi* specific antibodies each sample has to be analyzed by all three commercial assays in order to decide in a majority approach (i.e. two of three commercial assays detect the infection) which sample is reactive and contains *T. cruzi* specific antibodies.

According to the invention the composition of *Trypanosoma cruzi* specific polypeptides comprising 1F8, JL7 and at least one of the polypeptides selected from the group consisting of Cruzipain, KMP-11 and PAR2 shows a specificity around 99.8% which is comparable and in line with commercial assays (see Table 4, Example 5). We tested two kit variants, kit 1 comprising 1F8, JL7 and Cruzipain and kit 2 comprising 1F8, JL7 and Cruzipain and KMP-11. In addition, both kits/compositions show a superior dilution sensitivity when compared to three commercial anti-Chagas assays as can be seen from Example 6 and Table 5/FIG. 3.

The term composition means that isolated separate *T. cruzi* polypeptides are combined to an admixture. This term shall not include polypeptides that have been recombinantly expressed or synthesized (chemically produced) on one single chain of amino acids so that all polypeptides are located on just one polypeptide chain as a multi-antigen-fusion polypeptide. In other words, multi-epitope fusion antigens of several epitopes that naturally do not appear on a single polypeptide chain are excluded. Rather, each of the *T. cruzi* polypeptides 1F8, JL7 and at least one of the polypeptides selected from the group consisting of Cruzipain, KMP-11 and PAR2 are expressed on or chemically synthesized as separate polypeptide chains. In an embodiment the composition consists of three recombinantly or synthetically produced polypeptides specific for *T. cruzi*, wherein said polypeptides are 1F8, JL7, and Cruzipain. The composition is created by mixing the individual *T. cruzi* polypeptides in one vessel or tube resulting in a composition.

The composition can be liquid, i.e. the *T. cruzi* polypeptides are added to a mixture in a water or buffer soluble form. Suitable buffer ingredients are known to the person skilled in the art. Said composition may also be solid, i.e. it comprises the *T. cruzi* antigens in a lyophilized or otherwise dried form.

In an embodiment, said composition of polypeptides comprises a 1F8 amino acid sequence according to SEQ ID NO. 1, a JL7 sequence according to SEQ ID NO. 2 and the at least one of the polypeptides selected from the group consisting of Cruzipain, KMP-11 and PAR2 comprises at least one sequence selected from the group consisting of SEQ ID NO. 3 (Cruzipain), SEQ ID NO. 4 (KMP-11) and SEQ ID NO. 5 (PAR2).

In another embodiment, the composition of polypeptides comprises polypeptide 1F8, JL7 and Cruzipain. In yet another embodiment, said composition comprises polypeptides according to SEQ ID NOs. 1 (1F8), 2, (JL7) and 3 (Cruzipain). In a further embodiment, said composition consists of three polypeptides comprising SEQ ID NOs. 1 (1F8), 2, (JL7) and 3 (Cruzipain). In a further embodiment the part that is specific for *T. cruzi* consists of SEQ NOs. 1 (1F8), 2, (JL7) and 3 (Cruzipain). In another embodiment, said composition consists of polypeptides comprising SEQ ID NOs. 1 (1F8), 2, (JL7), 3 (Cruzipain) and 4 (KMP-11).

The expression "the part that is specific for *T. cruzi* consists of SEQ ID NO. 1 (or 2 or 3, etc.)" means that e.g. SEQ ID NO. 1 is the only polypeptide part derived from an antigen present in *T. cruzi* that is present on this polypeptide chain and that reacts with *T. cruzi*-specific antibodies. However, the addition of non-*T. cruzi*-specific linker or peptidic fusion amino acid sequences is possible as these sequences are not specific for *T. cruzi* and would not be recognized by a *T. cruzi*-specific antibody.

According to the invention also variants of the 1F8, JL7, Cruzipain, KMP-11 and PAR2 antigens according to SEQ ID NOs. 1, 2, 3, 4, or 5 are included in the composition. This applies also to the polypeptides 1F8, JL7 and Cruzipain present in a composition consisting of three *T. cruzi*-specific polypeptides. The term "variants" in this context relates to a protein or a protein fragment (i.e. a polypeptide or peptide) substantially similar to said protein. In particular, a variant may be an isoform which shows amino acid exchanges, deletions or insertions compared to the amino acid sequence of the most prevalent protein isoform. In one embodiment, such a substantially similar protein has a sequence similarity to the most prevalent isoform of the protein of at least 80%, in another embodiment at least 85% or at least 90%, in yet another embodiment at least 95%. The term "variant" also relates to a post-translationally modified protein such as a glycosylated or phosphorylated protein. According to the invention a variant classifies as such as long as the immunoreactivity in an in vitro diagnostic immunoassay is maintained, i.e. the variant is still able to bind and detect anti-*T. cruzi* antibodies present in a sample. A "variant" is also a polypeptide or antigen which has been modified for example by covalent attachment of a linker amino acid sequence, a label, a tag amino acid sequence or carrier moiety to the polypeptide or antigen.

The polypeptide composition according to the invention is soluble under physiological buffer conditions, as known to someone skilled in the art. The term "specific for *T. cruzi*" means that the polypeptides are capable of binding to or being recognized and bound by antibodies specific for *Trypanosoma cruzi* that are present in an isolated sample such as human sera.

All *T. cruzi* specific polypeptides according to the invention can be expressed as fusion proteins with non-*T. cruzi* specific polypeptide sequences such as folding helper molecules like chaperones. The goal of these fusion partners is to facilitate cloning, expression and purification of the analyte specific polypeptide. However, according to the invention the *T. cruzi* specific polypeptides can equally be produced as stand-alone polypeptides without any chaperone fusion partner. In an embodiment the individual polypeptides which form the composition of *T. cruzi* specific antigens according to the invention are produced without a chaperone fusion partner. Example 7 and Table 6 (FIG. 4) show that the antigenicity in an immunoassay for detecting *T. cruzi* specific antibodies is independent of the presence of a chaperone fusion partner for each antigen.

The invention also concerns a method of producing a soluble and immunoreactive composition of polypeptides suitable for detecting antibodies against *Trypanosoma cruzi*. All individual *T. cruzi* specific antigens were produced according to the method described in Examples 1 or 2. In an embodiment, said method comprises the steps of
a) culturing host cells transformed with an expression vector comprising operably linked a recombinant DNA molecule encoding a first *Trypanosoma cruzi* polypeptide 1F8,
b) expression of said *Trypanosoma cruzi* polypeptide and
c) purification of said *Trypanosoma cruzi* polypeptide
d) repeating steps a) to d) with an expression vector comprising operably linked a recombinant DNA molecule encoding a second *T. cruzi* polypeptide JL7
e) repeating steps a) to d) with an expression vector comprising operably linked a recombinant DNA molecule encoding a third *T. cruzi* polypeptide selected from the group consisting of Cruzipain, KMP-11 and PAR2
f) forming an admixture of *T. cruzi* polypeptides obtained in steps c), d) and e), thereby producing a soluble and immunoreactive composition of polypeptides suitable for detecting antibodies against *Trypanosoma cruzi*.

In an embodiment the above detailed method for producing a composition of polypeptides concerns a composition consisting of three recombinantly produced polypeptides. In this case step e) is repeated with an expression vector comprising operably linked a recombinant DNA molecule encoding a third *T. cruzi* polypeptide cruzipain.

Another aspect of the current invention is a method for detecting antibodies specific for *Trypanosoma cruzi* in an isolated sample wherein a composition of *Trypanosoma cruzi* polypeptides comprising polypeptides 1F8, JL7 and at least one of the polypeptides selected from the group consisting of Cruzipain, KMP-11 and PAR2 is used as a capture reagent and/or as a binding partner for said *Trypanosoma cruzi* antibodies.

In an embodiment the method for detecting antibodies specific for *Trypanosoma cruzi* in an isolated sample applies a composition consisting of three *Trypanosoma cruzi* polypeptides which are 1F8, JL7 and Cruzipain as described further above. In an embodiment polypeptide 1F8 comprises SEQ ID NO. 1, JL7 comprises SEQ ID NO. 2 and Cruzipain comprises SEQ ID NO. 3. In yet another embodiment 1F8 consists of SEQ ID NO. 1, JL7 consists of SEQ ID NO. 2 and Cruzipain consists of SEQ ID NO. 3. Said composition of *Trypanosoma cruzi* polypeptides for the above-described detection of *T. cruzi* specific antibodies can also be obtained by the method of production of polypeptides of the preceding paragraph. In a further aspect said method is suitable for detecting *T. cruzi* antibodies of all soluble immunoglobulin subclasses, including IgG and IgM as the most relevant subclasses for Chagas diagnostics.

Immunoassays for detection of antibodies are well known to everyone skilled in the art, and so are methods for carrying out such assays and practical applications and procedures. The composition of *T. cruzi* specific antigens according to the invention can be used to improve assays for the detection of anti-*T. cruzi* specific antibodies independently of the labels used and independently of the mode of detection (e.g., radioisotope assay, enzyme immunoassay, electrochemiluminescence assay, etc.) or the assay principle (e.g., test strip assay, sandwich assay, indirect test concept or homogenous assay, etc.). All biological liquids known to the expert can be used as samples for the detection of anti-*T. cruzi* antibodies. The samples usually used are body liquids like whole blood, blood sera, blood plasma, urine or saliva.

A further aspect of the invention is a method for detecting antibodies specific for *Trypanosoma cruzi* in an isolated sample said method comprising
a) forming an immunoreaction admixture by admixing a body fluid sample with a composition of *Trypanosoma cruzi* polypeptides as defined above or with a composition of *Trypanosoma cruzi* polypeptides obtained by the method described above
b) maintaining said immunoreaction admixture for a time period sufficient for allowing antibodies present in the body fluid sample against said composition of polypeptides sample to immunoreact with said composition of *Trypanosoma cruzi* polypeptides to form an immunoreaction product; and
c) detecting the presence and/or the concentration of any of said immunoreaction product.

In an embodiment said method for detecting antibodies specific for *Trypanosoma cruzi* in an isolated sample is carried out in a double antigen sandwich (DAGS) format. In such an assay the ability of an antibody to bind at least two different molecules of a given antigen with its two (IgG, IgA, IgE) or ten (IgM) paratopes is required and utilized. In said DAGS immunoassay the basic structures of the "solid phase antigen" and the "detection antigen" are essentially the same so that the sample antibody forms a bridge between two specific antigens. Both antigens therefore have to be either identical or immunologically cross-reactive so that one antibody is able to bind to both antigens. The essential requirement for performing such assays is that the relevant epitope or the relevant epitopes are present on both antigens. One of the two antigens can be bound to a solid phase and the other antigen carries a detectable label.

According to the invention the DAGS assay procedure comprises the following steps:
a) adding to an isolated sample a first composition of *Trypanosoma cruzi* polypeptides which can be bound directly or indirectly to a solid phase and each of said first *Trypanosoma cruzi* polypeptides carries an effector group which is part of a bioaffine binding pair, and a second composition of *Trypanosoma cruzi* polypeptides and each of said second *Trypanosoma cruzi* polypeptides carries a detectable label, wherein said first and second *Trypanosoma cruzi* polypeptides bind specifically to said anti-*Trypanosoma cruzi* antibodies, b) forming an immunoreaction admixture comprising the first *Trypanosoma cruzi* polypeptides, the sample antibody and the second *Trypanosoma cruzi* polypeptides wherein a solid phase carrying the corresponding effector group of said bioaffine binding pair is added before, during or after forming the immunoreaction admixture, c) maintaining said immunoreaction admixture for a time period sufficient for allowing *Trypanosoma cruzi* antibodies against said first and second *Trypanosoma cruzi* polypeptides in the body fluid sample to immunoreact with said first and second *Trypanosoma cruzi* polypeptides to form an immunoreaction product, d) separating the liquid phase from the solid phase e) detecting the presence of any of said immunoreaction product in the solid or liquid phase or both.

In an embodiment said first *Trypanosoma cruzi* polypeptide carries a biotin moiety as part of the bioaffine binding pair biotin/streptavidin, and said second *Trypanosoma cruzi* polypeptide is labeled with an electrochemiluminescent ruthenium complex.

Another embodiment of the invention is the use of a composition of *Trypanosoma cruzi* polypeptides comprising polypeptides 1F8, JL7 and at least one of the polypeptides selected from the group consisting of Cruzipain, KMP-11 and PAR2 in an in vitro diagnostic test for the detection of anti-*Trypanosoma cruzi* antibodies. In an embodiment the composition for use in an in vitro diagnostic test for the detection of anti-*Trypanosoma cruzi* antibodies consists of the three *T. cruzi* polypeptides 1F8, JL7 and Cruzipain. Said composition of *Trypanosoma cruzi* polypeptides can also be obtained by the method of production of polypeptides as described further above.

Yet another aspect of the current invention is a reagent kit for the detection of anti-*Trypanosoma cruzi* antibodies, comprising polypeptides 1F8, JL7 and at least one of the polypeptides selected from the group consisting of Cruzipain, KMP-11 and PAR2. In an embodiment the polypeptides present in said reagent kit or the detection of anti-*Trypanosoma cruzi* antibodies, consist of polypeptides 1F8, JL7 and Cruzipain. Said kit is useful for an in vitro diagnostic test for the detection of anti-*Trypanosoma cruzi* antibodies and may further contain controls and standard solutions in separate vials as well as additional reagents in one or more solutions or in lyophilized form with the common additives, buffers, salts, detergents etc. and instructions for use as known by the person skilled in the art. Also for the kit, said composition of *Trypanosoma cruzi* polypeptides can also be obtained by the method of production of polypeptides as described further above.

In yet another embodiment of the invention we could show that the reactivity of the *T. cruzi* antigen 1F8 is dependent on the presence of calcium ions. As described in Example 8/Table 7 (FIG. 8) the addition of calcium ions leads to a clear gain in immunological reactivity when 1F8 is part of the *T. cruzi* antigen composition. Furthermore, the addition of calcium ions to the assay buffer can reduce recovery-effects of plasma as sample material (i.e. $Ca^{2+}$ complexing-effects of anti-coagulants, e.g. Citrate, EDTA or Heparine in plasma-sampling tubes) when the 1F8 antigen, a calcium binding protein, is used in the *T. cruzi* antigen composition. The invention therefore also concerns a composition of polypeptides suitable for detecting antibodies against *Trypanosoma cruzi* in an isolated biological sample comprising polypeptides 1F8, JL7 and at least one of the polypeptides selected from the group consisting of Cruzipain, KMP-11 and PAR2 wherein said composition contains calcium ions in a concentration of 0.001 to 100 millimol per liter, in an embodiment 0.1 to 10 millimol per liter, in another embodiment 0.5 to 5 millimol per liter, in another embodiment 1 to 5 millimol per liter and in yet another embodiment 5 millimol per liter. Calcium may be added in the form of a water-soluble salt like e.g. calcium chloride. The addition of calcium ions as detailed above also applies to a composition of three polypeptides suitable for detecting antibodies against *Trypanosoma cruzi* in an isolated biological sample wherein the polypeptides are 1F8, JL7 and Cruzipain. In an embodiment polypeptide 1F8 comprises SEQ ID NO. 1, polypeptide JL7 comprises SEQ ID NO. 2 and polypeptide Cruzipain comprises SEQ ID NO. 3. In yet another embodiment said polypeptides 1F8, JL7 and Cruzipain consist of SEQ ID NOs. 1, 2 and 3, respectively.

The addition of calcium ions and the defined concentration ranges are also an embodiment for the kit described further above comprising polypeptides 1F8, JL7 and at least one of the polypeptides selected from the group consisting of Cruzipain, KMP-11 and PAR2 as well as for the kit with three *T. cruzi*-specific polypeptides consisting of 1F8, JL7 and Cruzipain. Said kits may contain calcium ions in concentration ranges as defined before, in an embodiment in a concentration of 0.1 to 10 millimol per liter.

The invention is further illustrated by the examples section. In particular, the examples illustrate that we have developed and generated variants of *T. cruzi* specific polypeptides which, when applied as a novel composition of at least three different antigens, in an embodiment consisting of three antigens, show superior results in an immunoassay for detecting *T. cruzi* specific antibodies with regard to specificity and sensitivity.

Example 1

Cloning and Purification of the *Trypanosoma cruzi* Antigens with Chaperone Fusion Synthetic genes encoding the *T. cruzi* antigens denoted in Table 1 with the prefix "EcSS" were purchased from Eurofins MWG Operon (Ebersberg, Germany). On the basis of the pET24a expression plasmid of Novagen (Madison, Wis., USA) the following cloning steps were performed. The vector was digested with NdeI and XhoI and a semisynthetic cassette comprising tandem-SlyD and the respective *T. cruzi* antigens were inserted. The insert of the resulting plasmid was sequenced and found to encode the desired fusion protein. The amino acid sequences of the *T. cruzi* polypeptides (SEQ ID NOs. 1-5) and the *E. coli* SlyD chaperone moiety (SEQ ID NO. 6) resulting in fusion proteins are shown in the sequence protocol of the present invention. Two SlyD units (tandem SlyD) were fused to the N-terminal end of the respective *T. cruzi* polypeptide. All recombinant *T. cruzi* fusion polypeptide variants contained a C-terminal hexahistidine tag (SEQ ID NO. 8) to facilitate Ni-NTA-assisted purification and refolding. SEQ ID NOs. are summarized in Table 1.

All *T. cruzi* chaperone fusion antigens were purified and refolded according to an identical protocol irrespective of the presence of cysteine residues in the particular polypeptide chain. *E. coli* BL21 (DE3) cells harboring the expression plasmid were grown in LB medium plus kanamycin (30 µg/ml) to an $OD_{600}$ of 1, and cytosolic overexpression was induced by adding isopropyl-β-D-thiogalactosid (IPTG) to a final concentration of 1 mM at a growth temperature of 37° C. 4 hours after induction, cells were harvested by centrifugation (20 min at 5000×g), frozen and stored at −20° C. For cell lysis, the frozen pellet was resuspended in 25 mM sodium phosphate pH 8.5, 6 mM $MgCl_2$, 10 U/ml Benzonase®, 1 tablet Complete® and 1 tablet Complete® EDTA-free per 50 ml of buffer (protease inhibitor cocktail) and the resulting suspension was lysed by high pressure homogenization. The crude lysate was supplemented up to 7 M GuHCl (guanidine hydrochloride), 50 mM sodium phosphate, 5 mM imidazole and stirred for one hour. After centrifugation the supernatant was applied onto a Ni-NTA (nickel-nitrilotriacetate) column pre-equilibrated in buffer A (50 mM sodium phosphate pH 8.5, 7.0 M GuHCl, 5 mM imidazole). In order to prevent premature disulfide bridging and disulfide shuffling, particularly for SS-C-cruzipain, 5 mM TCEP was included in the washing buffer as a reducing agent which is compatible with metal chelate columns. After a washing step, the chaotropic buffer A was displaced by 50 mM sodium phosphate pH 8.5, 100 mM sodium chloride, 10 mM imidazole, 5 mM TCEP, 1 tablet Complete® EDTA-free per 50 ml of buffer (protease inhibitor cocktail) in order to induce the conformational refolding of the matrix bound protein. Subsequently, the oxidative folding (i.e. the oxidative bridging of the cysteine residues) was induced by washing with 50 mM sodium phosphate pH 8.5, 100 mM sodium chloride, 10 mM imidazole, 1 tablet Complete® EDTA-free per 50 ml of buffer. Due to the high effective concentration of divalent $Ni^{2+}$ ions, the formation of disulfide bridges within the matrix-bound fusion protein is a very fast process. Prior to elution, the imidazole concentration was raised to 40 mM in order to remove contaminant proteins. The native fusion proteins were then eluted by applying an imidazole concentration of 250 mM in 50 mM sodium phosphate pH 8.5, 100 mM sodium chloride. Protein containing fractions were assessed for purity by SDS-PAGE and pooled. Finally, the proteins were subjected to size exclusion chromatography and the protein-containing fractions was pooled and concentrated.

Example 2

Cloning and Purification of the *Trypanosoma cruzi* Antigens without Chaperone Fusion Synthetic genes encoding the *T. cruzi* antigens as listed in Table 1 were purchased from Eurofins MWG Operon (Ebersberg, Germany). On the basis of the pET24a expression plasmid of Novagen (Madison, Wis., USA) the following cloning steps were performed. For the *T. cruzi* antigens 1F8, JL7, KMP-11 or C-Cruzipain the vector was digested with Nde I or BamH1, respectively, and Xho I and a cassette comprising the respective *T. cruzi* antigens (SEQ ID NOs. 1-4) were inserted. The insert of the resulting plasmid was sequenced and found to encode the desired protein. The amino acid sequences of the resulting proteins are shown in the sequence protocol of the present invention. All recombinant *T. cruzi* polypeptide variants contained a C-terminal hexahistidine tag to facilitate Ni-NTA-assisted purification and refolding. SEQ ID NOs. are summarized in Table 1.

All *T. cruzi* antigens without chaperone fusion were purified according to the following protocol. *E. coli* BL21 (DE3) cells harboring the expression plasmid were grown in LB medium plus kanamycin (30 µg/ml) to an $OD_{600}$ of 1, and cytosolic overexpression was induced by adding isopropyl-β-D-thiogalactosid (IPTG) to a final concentration of 1 mM at a growth temperature of 37° C. 4 hours after induction, cells were harvested by centrifugation (20 min at 5000×g), frozen and stored at −20° C. For cell lysis, the frozen pellet was resuspended in 25 mM sodium phosphate pH 8.5, 6 mM $MgCl_2$, 10 U/ml Benzonase®, 1 tablet Complete® and 1 tablet Complete® EDTA-free per 50 ml of buffer (protease inhibitor cocktail) and the resulting suspension was lysed by high pressure homogenization. The crude lysate was supplemented up to 50 mM sodium phosphate, 10 mM imidazole. After centrifugation the supernatant was applied onto a Ni-NTA (nickel-nitrilotriacetate) column pre-equilibrated in buffer A (50 mM sodium phosphate pH 8.5, 100 mM sodium chloride, 10 mM imidazole). Prior to elution, the imidazole concentration was raised to 40 mM in order to remove contaminant proteins. The proteins were then eluted by applying an imidazole concentration of 250 mM. Finally, the proteins were subjected to size exclusion chromatography and the protein-containing fractions was pooled and concentrated.—In Table 1, EcSS or SS as prefix denotes a tandem SlyD moiety which is N-terminally fused to the *T. cruzi* polypeptide.

TABLE 1

*T. cruzi* antigens obtained according to Examples 1 and 2

| *T. cruzi* antigen | Comprising Chagas antigen SEQ ID NO. |
|---|---|
| EcSS-1F8 (Cys) | 1 |
| EcSS-1F8 (Cys residues replaced by Ala) | 1 |
| EcSS-JL7 | 2 |
| EcSS-C-Cruzipain | 3 |
| EcSS-KMP11 | 4 |
| EcSS-C-PAR2 | 5 |
| 1F8 | 1 |
| JL7 | 2 |
| C-Cruzipain | 3 |
| KMP-11 | 4 |

Example 3

Coupling of Biotin and Ruthenium Moieties to *T. cruzi* Antigens

The lysine ε-amino groups of the recombinant proteins were modified at protein concentrations of ~10 mg/ml with N-hydroxy-succinimide activated biotin and ruthenium labels, respectively. The label/protein molar ratio varied from 3:1 to 30:1, depending on the respective protein. The reaction buffer was 50 mM potassium phosphate (pH 8.5), 150 mM KCl, 0.5 mM EDTA. The reaction was carried out at room temperature for 30 minutes and stopped by adding buffered L-lysine to a final concentration of 10 mM. After the coupling reaction, unreacted free label was removed by passing the crude protein conjugate over a gel filtration column (Superdex 200 HI Load).

Example 4

Assessment of the Immunological Reactivity of the Recombinant *T. cruzi* Antigens in an Immunodiagnostic Test; Detection of Anti-*T. cruzi* Antibodies in Human Sera The immunological reactivity of the different proteins was assessed in an automated Cobas® e601 analyzer (Roche Diagnostics GmbH). Measurements were carried out in the double antigen sandwich format. Thereby, the biotin-conjugate (i.e. the capture antigen) is immobilized on the surface of a streptavidin-coated magnetic bead, whereas the detection-antigen bears a complexed ruthenium cation as the signaling moiety. Signal detection in Cobas® e601 is based on electrochemiluminescence.

In the presence of a specific immunoglobulin analyte, the chromogenic ruthenium complex is bridged to the solid phase and emits light at 620 nm after excitation at a platinum electrode. The signal output is in arbitrary light units. Measurements were performed with anti-*T. cruzi* positive and negative human serum and plasma samples purchased from several sources. All samples were tested with three commercially available Chagas assays (Architect Chagas from Abbott Laboratories, bioelisa Chagas from Biokit S.A., NovaLisa Chagas IgG ELISA from NovaTec) according to the instructions of the respective manufacturer.

The Architect Chagas assay uses several multi-epitope fusion polypeptides each of which comprises several recombinant *T. cruzi* polypeptides that contain the antigens PEP-2, TcD, TcE, TcLo1.2, TcR27, FCaBP (=1F8), TcR39, FRA (=JL7), SAPA and MAP, resulting in ten different antigens. The bioelisa Chagas uses recombinant antigens PEP-2, TcD, TcE and TcLo1.2. The NovaLisa Chagas IgG ELISA uses the multi-epitope fusion polypeptide TcF which comprises the antigens PEP-2, TcD, TcE and TcLo1.2. Note that within the *T. cruzi* antigens nomenclature identical or very similar antigens often carry several synonyms, such as e.g. FCaBP=1F8 or PEP-2 is synonymous to B13 and Ag2 and TcR39, for review, see e.g. Silveira et al, Trends in Parasitol. 2001, Vol. 17 No. 6 or Marcipar et al., Current Topics in Trop. Med 16 Mar. 2012, p. 273-398.

The recombinant *T. cruzi* antigen variants according to the invention were assessed pairwise in a double antigen sandwich (DAGS) immunoassay format. For instance, a SS-1F8-biotin conjugate was assessed together with a SS-1F8-ruthenium complex conjugate at a concentration of 800 ng/ml each in assay buffer containing 50 mM MES (pH 6.5), 150 mM NaCl, 0.1% polidocanol, 0.2% bovine albumin, 0.01% N-methylisothiazolon, 0.1% Oxy-Pyrion. In all measurements, chemically polymerized and unlabeled EcSlyD-EcSlyD (SS) was implemented in large excess (20 µg/ml) in the reaction buffer as an anti-interference substance to avoid immunological cross reactions via the chaperone fusion unit. Anti-*T. cruzi* negative human sera were used as controls. The used sample volume was 49 µl.

sufficiently discriminate between Chagas positive and negative specimens. All results judged to be positive are written in bold type letters.

It is obvious that the reactivity of the *T. cruzi* antigen variants is strongly dependent on the individual patient serum. All antigen variants according to the invention exhibit significant antigenicity.

Table 3 (FIG. 2) shows results of specimens tested with three commercially available Chagas assays (Architect Chagas, bioelisa Chagas and Novalisa Chagas IgG ELISA; ingredient antigens see above). All samples are determined to be Chagas-positive according to a majority approach. This means that if two out of three assays provide a positive result and the third assay is negative the sample is judged as positive because the majority of assay results (2:1) is positive. All individual results judged to be positive are printed in bold type letters.

As can be seen from Table 3 there are only a few specimens reacting with all recombinant antigens described in the present invention. Although EcSS-C-Cruzipain was the only antigen able to react with all Chagas positive samples investigated in Table 3 (FIG. 2) a reliable detection of Chagas antibodies in human sera needs a composition comprising more than one specific antigen.

Example 5

Specificity of Recombinant *T. cruzi* Antigen Mixtures

In order to assess the specificity (i.e. the true negative rate) of afore mentioned recombinant Chagas antigens two prototype kits with different antigen mixtures were generated. Kit variant 1 was built up of EcSS-1F8, EcSS-JL7 and EcSS-C-Cruzipain. Kit variant 2 included EcSS-KMP-11 additionally.

The biotin and the ruthenium conjugates of the polypeptide variants of *T. cruzi* antigens were applied at concentrations of 100 ng/ml each. In all measurements, chemically polymerized and unlabeled anti-interference reagent EcSlyD-EcSlyD (SS) was implemented in large excess (20 µg/ml) in the reaction buffer. The used sample volume was 30 µl.

TABLE 4

Specificity of recombinant *T. cruzi* antigen mixtures in comparison with commercial anti-Chagas assays

| Specimens | No. | Kit variant 1<br>EcSS-1F8<br>EcSS-JL7<br>EcSS-C-Cruzipain<br>No. reactive/specificity | Kit variant 2<br>EcSS-1F8<br>EcSS-JL7<br>EcSS-C-Cruzipain<br>EcSS-KMP11<br>No. reactive/<br>specificity | Architect Chagas<br>specificity | bioelisa Chagas<br>specificity |
|---|---|---|---|---|---|
| blood donors | n = 494 | 1*/99.80% | 1*/99.80% | 99.92%-99.98%** | 97.4%-99.5%** |

*>sixfold average of human normal sera
**package insert

In Table 2 (FIGS. 1A and 1B), the immunological activity of the *T. cruzi* antigen chaperone fusion variants (see sequence listing and summary of sequences, supra) is shown. The first five samples are normal human sera, the samples below are proven *T. cruzi*-antibody positive samples. The working cut-off for the assessment of the described Chagas antigens was arbitrarily chosen as the six-fold average of the five normal human sera in order to 494 blood donors from the Bavarian Red Cross (normal samples) were tested with both of the kit variants and the results are summarized in Table 4 above.

Only one out of 494 samples was reactive with both kit variants of the present invention. This sample was further investigated by the NovaLisa Chagas IgG ELISA from NovaTec with a non-reactive finding. The resulting specificity of 99.80% is in line with other commercial anti-Chagas assays.

Example 6

Sensitivity of Recombinant *T. cruzi* Antigen Mixtures

The sensitivity (i.e. the true positive rate) of the two kit variants described in example 5 was compared to two commercially available Chagas assays (bioelisa Chagas from Biokit S.A., Ortho *T. cruzi* ELISA Test System from Ortho-Clinical Diagnostics) by measurements of linear dilution-rows of the two different WHO standards for Chagas antibodies (TcI and TcII, TcI=*T. cruzi* genotype I; TcII= *T. cruzi* genotype II) in human serum matrix (Table 5, FIG. 3). All results judged to be positive are printed in bold type letters.

There is no significant difference between the kit variants 1 and 2 of the present invention in dilution sensitivity experiments. However, both kit variants are 4 to 6 linear dilutions steps more sensitive than the competitor assays bioelisa Chagas, the Ortho *T. cruzi* ELISA or the Architect Chagas. The ingredient *T. cruzi* antigens for bioelisa Chagas and the Architect Chagas are described in Example 4. The Ortho *T. cruzi* ELISA is based on a *T. cruzi* cell lysate and does not contain recombinant antigens.

An increased dilution sensitivity as achieved by the current invention means that also at very low concentration of antibodies the presence of the antibodies can be reliably detected.

Example 7

Comparison of the Immunological Reactivity of Recombinant *T. cruzi* Antigens with and without Chaperone Fusion The immunological reactivity of the recombinant *T. cruzi* antigens with chaperone fusion was shown in the examples before. In order to show that the immunological reactivity of the *T. cruzi* antigens according to the invention is independent of the presence of a fusion partner the recombinant *T. cruzi* antigens without chaperone fusion as described in example 2 were also assessed concerning their immunological reactivity. Table 6 (FIG. 4) summarizes the results of measurements.

The biotin and the ruthenium conjugates of the polypeptide variants of *T. cruzi* antigens were applied at concentrations of 100 ng/ml each. In all measurements, chemically polymerized and unlabeled anti-interference reagent EcSlyD-EcSlyD (SS) was implemented in large excess (20 μg/ml) in the reaction buffer. The used sample volume was 30 μl.

As can be concluded from the measuring data of Table 6 (FIG. 4) the *T. cruzi* antigen variants without a chaperone fusion partner also exhibit significant antigenicity. The differences in signal observed can be explained by different labeling rates as a consequence of different numbers of accessible lysine residues (with or without SlyD-fusion). Another aspect might be different sites of labeling which may lead to different impairment of epitopes. Additionally, the molar concentrations of the antigens without chaperone fusion are higher than their counterparts containing said fusion partner. In summary, the suitability of the *T. cruzi* polypeptides for detecting *T. cruzi* antibodies is independent of a chaperone fusion partner. The mere *T. cruzi* specific polypeptide antigen sequence is necessary to detect *T. cruzi*-specific antibodies.

Example 8

Influence of Calcium Ions on the Immunological Reactivity of the Recombinant *T. cruzi* Antigen 1F8

In order to investigate the influence of calcium ions on immunological reactivity of the recombinant *T. cruzi* antigen 1F8—also called Tc24, Tc28 or FCaBP (flagellar calcium binding protein) a known calcium binding protein of *Trypanosoma cruzi*—, the assay buffer as described in example 4 was supplemented with calcium chloride at a concentration of 1 mM. The biotin and the ruthenium conjugates of EcSS-1F8 were applied at concentrations of 200 ng/ml each. In all measurements, chemically polymerized and unlabeled anti-interference reagent EcSlyD-EcSlyD (SS) was implemented in large excess (20 μg/ml) in the reaction buffer. The used sample volume was 30 μl.

Most of the sera of Chagas infected patients in Table 7 (FIG. 5) showed a clear gain in immunological reactivity of the *T. cruzi* 1F8 antigen due to addition of calcium ions to the assay buffer. For some Chagas positive sera the signal could be doubled. The differences in signal observed can be explained by heterogeneous patterns of immune answers of individual patients as also shown in Table 2 (FIGS. 1A and 1B).

The gain in immunological reactivity of the *T. cruzi* 1F8 antigen due to addition of calcium ions could also be observed when the polypeptide composition according to the invention consisting of three polypeptides 1F8, JL7 and Cruzipain was applied (data not shown).

---

The invention claimed is:

1. A composition of polypeptides suitable for detecting antibodies agains *Trypanosoma cruzi* in an isolated biological sample, said composition comprising three recombinantly or synthetically produced polypeptides specific for *Trypanosoma cruzi*, wherein said polypeptides are selected from the group consisting of SEQ ID NO:1, SEQ ID NO:2 and SEQ ID NO:3.

2. A composition of polypeptides according to claim 1 wherein said composition comprises calcium ions in a concentration of 0.1 to 10 millions per liter.

3. A reagent kit for the detection of anti-*Trypanosoma cruzi* antibodies, comprising a composition of *Trypanosoma cruzi* polypeptides according to claim 1.

* * * * *